US007138545B2

(12) United States Patent
Murray et al.

(10) Patent No.: US 7,138,545 B2
(45) Date of Patent: Nov. 21, 2006

(54) METAL SALTS

(75) Inventors: James Murray, Aberdeen (GB); Edmund Austin Tobin, Aberdeenshire (GB); Stephen Geoffrey Warren, Herts (GB)

(73) Assignees: Johnson Matthey Public Limited Company, London (GB); Aubin Limited, Ellon (GB)

( * ) Notice: Subject to any disclaimer, the term of this patent is extended or adjusted under 35 U.S.C. 154(b) by 0 days.

(21) Appl. No.: 10/520,226

(22) PCT Filed: Jul. 2, 2003

(86) PCT No.: PCT/GB03/02843

§ 371 (c)(1),
(2), (4) Date: Aug. 17, 2005

(87) PCT Pub. No.: WO2004/005234

PCT Pub. Date: Jan. 15, 2004

(65) Prior Publication Data

US 2006/0009649 A1    Jan. 12, 2006

(30) Foreign Application Priority Data

Jul. 4, 2002    (GB) ................. 0215384.9

(51) Int. Cl.
*C07C 53/10*    (2006.01)
*C07C 53/06*    (2006.01)
(52) U.S. Cl. ...................... 562/607; 562/609
(58) Field of Classification Search ...................... None
See application file for complete search history.

(56) References Cited

U.S. PATENT DOCUMENTS

| 4,440,649 A | 4/1984 | Loftin et al. |
| 5,139,981 A * | 8/1992 | Kurland ....................... 502/11 |
| 6,177,014 B1 | 1/2001 | Potter et al. |

FOREIGN PATENT DOCUMENTS

EP    0 572 113 A1    12/1993

* cited by examiner

*Primary Examiner*—Paul A. Zucker
(74) *Attorney, Agent, or Firm*—RatnerPrestia

(57) ABSTRACT

Alkali metal carboxylate salt brines, such as cesium formate brine, are used in oil and gas drilling procedures. Contamination with chloride ions can be controlled by treatment with a silver salt solution, and removing silver chloride formed. High density brines can be obtained, suitable for re-use.

15 Claims, No Drawings

METAL SALTS

CROSS-REFERENCE TO RELATED APPLICATIONS

This application is the U.S. national phase application of International Application No. PCT/GB03/002843, filed Jul. 2, 2003, and claims priority of British Patent Application No. 0215384.9, filed Jul. 4, 2002.

FIELD OF THE INVENTION

The present invention concerns improvements in metal salts, more especially concerns the removal of certain ions from aqueous solutions.

BACKGROUND OF THE INVENTION

It is commonplace in drilling for oil and gas, to use fluids such as brines as well servicing fluids. In general, such fluids have desirably a high density. In particular, highly concentrated alkali metal salts of carboxylic acids have been developed for use in oil and gas well drilling and completion operations. Such a fluid may be based upon cesium and potassium salts such as formates, which can provide brines of specific gravity values of 1.6 to 2.3, depending upon solution concentrations.

During use of such brines, they may be contaminated with sodium chloride from sea water or from water or salt entrained within the rock and mud during application in the well bore. Chloride ions can cause severe corrosion of steel pipework and additionally may be incompatible with the rock matrix, causing damage to or near the well bore area. Such problems may result in users of such brines refusing to re-use chloride-contaminated brines. A charge of cesium formate solution for use as an oil field brine may cost in the order of $10M, so there is considerable need to improve the prospects for recycling such a brine.

Further, if a diluted brine is returned to high density by evaporation of water, any chloride concentration will increase by this process, thereby rendering the brine less suitable for re-use.

SUMMARY OF THE INVENTION

Accordingly, the present invention can be applied to removal of chloride from brine both caused by contamination in use or caused by a concentration process such as evaporation, and throughout this description and claims the term "brine" is to be understood as including brines which have been concentrated.

The present invention provides a method of treating an alkali metal carboxylate salt brine contaminated with chloride ion, comprising mixing such contaminated brine with a solution of a silver salt, especially silver nitrate, causing silver chloride to be formed and separating the silver chloride from the residual brine.

The invention may also be expressed as a method of use of an alkali metal carboxylate salt brine, comprising the recovery of used brine contaminated with chloride ion, treating the recovered brine with a solution of a silver salt, especially silver nitrate, causing silver chloride to be formed and separating the silver chloride from the brine, and re-using the brine. Desirably, the brine comprises cesium as the majority alkali metal by weight, and formate, acetate or other species, as the salt anion. The brine may comprise a significant proportion of other alkali metals, and may therefore contain mixtures of alkali metal carboxylates. Further, the brine may comprise one or more polymers or other components which are adjuvants and provide desirable properties to the brine or avoid disadvantages.

The preferred silver salt is silver nitrate, and for ease of description, all references hereinafter will be to silver nitrate.

DETAILED DESCRIPTION OF THE INVENTION

Since the specific gravity of the brine is extremely important, it is desirable to minimise any loss of specific gravity by undue dilution during the treatment. Accordingly, it is desirable to use silver nitrate solutions containing at least 200 g/l of $AgNO_3$, more preferably at least 300 g/l $AgNO_3$ and most preferably at least about 800 g/l. At room temperature, saturation concentrations are about 1400 g/l $AgNO_3$. The silver nitrate solution may contain other components which do not significantly adversely interfere with the method of the invention, or the performance of the brine. The silver nitrate solution is conveniently a product stream from a process involving the manufacture of high purity silver nitrate. This can provide economies arising from heat and water savings and other processing costs.

The treatment of the invention is conveniently carried out at room temperature, but may be carried out at higher or lower temperatures. It will be borne in mind that solubility decreases with decreasing temperature, and crystallisation may occur. Depending upon the chloride concentration, it may be necessary to cool the brine to about 0° C., to facilitate the removal of sufficient nitrate salts formed as a by-product to create a stable solution that can be supplied and used in winter conditions.

Conveniently, silver chloride may be removed from the brine by filtration. This is particularly applicable because of the relatively high value of the silver chloride. Other methods for separation may be used, however, such as hydrocyclones or centrifuges, and where applicable or desirable, polymeric materials may be added to enhance separation.

The treatment may be carried out in a two-step process, or, in a preferred embodiment, in a single step process. Desirably, at least a 90% stoichiometric quantity of silver nitrate is used, relative to chloride ion, in the treatment. More desirably, the quantity of silver nitrate is from approximately 95% to approximately 112% stoichiometric, for brines containing 8.47 to 13.5 g/l chloride. If the brine has other chloride contents or components, the stoichiometric adjustment may differ, which can be established by trial and error.

The recovered silver chloride may carry entrained by-products such as silver formate and cesium nitrate. Under preferred conditions, these are minimised and removed to permit the production of a re-usable brine. By washing and crystallisation, silver chloride crystals may be obtained and the silver value recovered in conventional ways by conversion to other compounds or silver metal, using methods available to the person of ordinary skill in the art. In general, therefore, it is preferred to separate the silver chloride by filtration, but conventional washing of the solids is not desirable if it causes undue dilution of the filtrate. Entrained cesium formate in the filtered precipitate may be washed out subsequently, using water, and cesium nitrate may also be recovered if desired.

The skilled person may use the information herein to optimise the process, using conventional techniques.

The invention may be further understood with reference to the following Examples.

EXAMPLE 1

Stoichiometric Additions of AgNO₃

200 ml samples of a used cesium formate brine, containing 1587 g/l cesium formate, 13.53 g/l chloride, 0.720 wt % sodium and 2.63 wt % potassium were used for all tests described. Desirably, the chloride level will be reduced below 1 g/l, more preferably 0.3–0.7 g/l.

In the first Example, stoichiometric amounts of $AgNO_3$ solution are added with stirring, to the brine, at room temperature and at differing concentrations:

| $AgNO_3$ concn. (g/l) | 150 | 200 | 600 | 918 | 1366 |
|---|---|---|---|---|---|
| Volume added (ml) | 87.6 | 65.7 | 21.6 | 14.5 | 9.5 |
| Cl⁻ concn. (g/l) (all concentrations in g/l normalised to 200 ml) | 0.50 | 0.64 | 0.72–0.99 | 1.0 | 1.78 |
| Specific gravity | 1.848 | 1.913 | 2.084 | 2.117 | 2.129 |

In order to produce a product brine having Cl⁻ concentration of approximately 0.5 g/l, combined with a specific gravity of not less than 2.0, a second stage treatment with $AgNO_3$ was undertaken, with the following results:

| | | | |
|---|---|---|---|
| First stage product Cl⁻ (g/l normalised) | 0.99 | 1.00 | 1.78 |
| $AgNO_3$ stoichiometry (%) | 50 | 50 | 80 |
| $AgNO_3$ concn. (g/l normalised) | 200 | 90 | 200 |
| Final Cl⁻ concn. (g/l normalised) | 0.54 | 0.51 | 0.44 |
| Overall $AgNO_3$ stoichiometry (%) | 103.2 | 103.4 | 110.0 |
| Specific gravity | 2.055 | 2.077 | 2.057 |

After first and second stages, the deposits formed in the brine were filtered off.

EXAMPLE 2

Single Stage Chloride Removal

The identical cesium formate brine as in Example 1 was used in further tests, using differing stoichiometries:

| Test No. | 1 | 2 | 3 |
|---|---|---|---|
| $AgNO_3$ stoichiometry (%) | 107 | 110 | 116 |
| Vol. $AgNO_3$ soln. added (ml) | 10.2 | 10.4 | 11 |
| Cl⁻ concn. (g/l normalised) | 0.58 | 0.35 | <0.01 |
| Specific gravity | 2.111 | 2.122 | 2.095 |

Tests 1 and 2 proceeded satisfactorily at room temperature. It was assessed in Test 3 that excess silver was being dissolved and a post-treatment of heating the product brine to 95° C. was incorporated, to remove the silver in solution.

A further post treatment of cooling to approximately 0° C. overnight followed by filtration, was found to remove a large proportion of by-product cesium nitrate, leaving a stable clear solution at room temperature.

EXAMPLE 3

Singe Stage Chloride Removal from a K/Cs Formate Brine 200 ml samples of a potassium/cesium formate brine, containing 497 g/l formate and 8.47 g/l chloride, 0.675 wt % sodium, 12.56 wt % potassium and 33.9 wt % cesium were used for all the tests described in this Example 3. Desirably, the chloride level will be reduced such that it lies in the range 0.7 to 1.0 g/l.

An orthogonal array of sixteen tests in which different concentrations and stoichiometric amounts of $AgNO_3$ are added at different temperatures, with different stirring rates, addition rates and residence times is shown below. In the tests in this Example, the reactants were stirred with an IKA Werke RCT Basic stirrer, using either a "Slow" setting (setting 4) or a "Fast" setting (setting 7). Addition rate was either "Slow" or "Fast", corresponding to a 15 minute addition time or a 30 second addition time, respectively. Residence times are the times from addition of the last drop of $AgNO_3$ to the beginning of filtration, and "Short" means 5 minutes and "Long" means 30 minutes.

| $AgNO_3$ conc. (g/l) | Stoichio-metry (%) | Temp-erature (° C.) | Stir Rate | Addition Rate | Residence Time | Norm. Cl⁻ conc. (g/l) | Specific Gravity |
|---|---|---|---|---|---|---|---|
| 600 | 95 | 25 | Fast | Fast | Short | 0.68 | 1.859 |
| 600 | 100 | 25 | Slow | Fast | Long | 0.81 | 1.867 |
| 600 | 105 | 35 | Fast | Slow | Long | 0.01 | 1.847 |
| 600 | 110 | 35 | Slow | Slow | Short | 0.38 | 1.848 |
| 800 | 95 | 35 | Slow | Fast | Long | 1.61 | 1.867 |
| 800 | 100 | 35 | Fast | Fast | Short | 0.42 | 1.871 |
| 800 | 105 | 25 | Slow | Slow | Short | 0.71 | 1.856 |
| 800 | 110 | 25 | Fast | Slow | Long | 0.01 | 1.851 |
| 1000 | 95 | 25 | Slow | Slow | Long | 1.86 | 1.856 |
| 1000 | 100 | 25 | Fast | Slow | Short | 0.41 | 1.857 |
| 1000 | 105 | 35 | Slow | Fast | Short | 1.37 | 1.871 |
| 1000 | 110 | 35 | Fast | Fast | Long | 0.01 | 1.868 |
| 1200 | 95 | 35 | Fast | Slow | Short | 0.87 | 1.884 |
| 1200 | 100 | 35 | Slow | Slow | Long | 1.84 | 1.886 |
| 1200 | 105 | 25 | Fast | Fast | Long | 0.14 | 1.871 |
| 1200 | 110 | 25 | Slow | Fast | Short | 3.26 | 1.865 |

By following the orthogonal matrix, it can be demonstrated that the chloride level can be reduced from 8.47 g/l to between 3.26 and <0.1 g/l by the addition of $AgNO_3$ under various conditions.

Analysis of the chloride levels observed by following the orthogonal matrix suggests that the stirring rate, concentration and stoichiometry of the $AgNO_3$ added, are the most significant factors that determine the post-treatment chloride level in descending order of importance. In particular, a fast stirring rate is highly desirable for efficient AgCl precipitation as the formate reduction of silver side reaction is minimised. The temperature, addition rate and residence time appear to be less significant factors.

To validate the conclusions drawn from the orthogonal array, a further three confirmation tests were designed specifically to reduce the post-treatment chloride level to 0.85, 0.65 and 0.45 g/l. The same brine was treated at 35° C., with the $AgNO_3$ added slowly with fast stirring before a long residence time.

| Test No. | 1 | 2 | 3 |
|---|---|---|---|
| AgNO$_3$ stoichiometry (%) | 95 | 95 | 100 |
| AgNO$_3$ concentration (g/l) | 1200 | 800 | 1000 |
| Target Cl$^-$ level | 0.85 | 0.65 | 0.45 |
| Cl$^-$ concentration (normalised, g/l) | 0.88 | 0.66 | 0.37 |
| SG | 1.890 | 1.874 | 1.884 |

The most AgNO$_3$ efficient reduction in Cl$^-$ level from 8.47 to <1 g/l and the lowest amount of water added occurs in Test 1.

The invention claimed is:

1. A method of treating an alkali metal carboxylate salt brine contaminated with chloride ion, comprising the steps of admixing the contaminated brine with a solution of a silver salt causing silver chloride to be formed in a reaction mixture and separating the silver chloride from the residual brine.

2. A method according to claim 1, wherein the brine comprises cesium or cesium and potassium as the alkali metal(s) and formate, acetate or other species as the salt anion.

3. A method according to claim 1, wherein the silver salt is silver nitrate and the concentration of the solution is at least 800 g/l AgNO$_3$.

4. A method according to claim 1, wherein the silver salt is silver nitrate and the method further comprises the steps of cooling the reaction mixture then removing by-product alkali metal nitrate.

5. A method according to claim 1, carried out such that the residual brine has a specific gravity of not less than 1.6.

6. A method according to claim 1, wherein the silver salt is silver nitrate and silver nitrate is used in a quantity of from 95 to 112% of stoichiometric.

7. A method of use of an alkali metal carboxylate salt brine, comprising the recovery of used or concentrated brine contaminated with chloride ion, treating the recovered brine with a solution of a silver salt causing silver chloride to be formed, separating the silver chloride from the brine, and re-using the brine.

8. A method according to claim 1, wherein the silver salt is silver nitrate.

9. A method according to claim 2, wherein the silver salt is silver nitrate and the concentration of the solution is at least 800 g/l AgNO$_3$.

10. A method according to claim 4, wherein the cooling step comprises cooling the reaction mixture to about 0° C.

11. A method according to claim 2, wherein the silver salt is silver nitrate and the method further comprises the steps of cooling the reaction mixture then removing by-product alkali metal nitrate.

12. A method according to claim 11, wherein the cooling step comprises cooling the reaction mixture to about 0° C.

13. A method according to claim 2, carried out such that the residual brine has a specific gravity of not less than 1.6.

14. A method according to claim 2, wherein the silver salt is silver nitrate and silver nitrate is used in a quantity of from 95 to 112% of stoichiometric.

15. A method according to claim 7, wherein the silver salt is silver nitrate.

* * * * *